US009745618B2

(12) United States Patent
Johnson et al.

(10) Patent No.: US 9,745,618 B2
(45) Date of Patent: Aug. 29, 2017

(54) PHOTOBLOCKED PROBES AND METHODS FOR SEQUENTIAL DETECTION OF NUCLEIC ACIDS

(71) Applicant: Roche Molecular Systems, Inc., Pleasanton, CA (US)

(72) Inventors: Jenny A Johnson, Castro Valley, CA (US); Stephen G Will, Oakland, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 203 days.

(21) Appl. No.: 14/548,197

(22) Filed: Nov. 19, 2014

(65) Prior Publication Data

US 2016/0138092 A1    May 19, 2016

(51) Int. Cl.
*C12Q 1/68* (2006.01)
*C12N 15/11* (2006.01)
*C07H 21/00* (2006.01)

(52) U.S. Cl.
CPC .......... *C12Q 1/6818* (2013.01); *C07H 21/00* (2013.01); *C12Q 1/6832* (2013.01); *C12Q 2561/101* (2013.01)

(58) Field of Classification Search
None
See application file for complete search history.

(56) References Cited

U.S. PATENT DOCUMENTS

| 5,556,961 A | 9/1996 | Foote et al. |
| 5,763,599 A | 6/1998 | Pfleiderer et al. |
| 6,017,758 A | 1/2000 | Haselton, III et al. |
| 2001/0038070 A1 | 11/2001 | Hausch et al. |
| 2008/0009007 A1 | 1/2008 | Lyle et al. |

FOREIGN PATENT DOCUMENTS

| CN | 103993101 A | 8/2014 |
| CN | 104046704 A | 9/2014 |

OTHER PUBLICATIONS

Ahern, The Scientist 9 (15), 20 (1995).*
Ghosn, Photochem. Photobiol. 2005, 81, 953-959.
Bochet, Tet. Lett., 2000, 41, 6341-6346.
Bochet, J. Chem. Soc., Perkin Trans. 1, 2002, 125-142.
Lemieux, Angew. Chem., 2006, 118, 6974-6978.
Li, PNAS, 2003, 100(2), 414-419.
Yu, Org. Soc. Rev., 2010, 39, 464-473.
Young, Chem. Comm., 2008, 4, 462-464.

* cited by examiner

*Primary Examiner* — James Martinell
(74) *Attorney, Agent, or Firm* — David J. Chang

(57) ABSTRACT

Photoblocked probes are disclosed including a specific hydrolysis probe having a first nucleic acid sequence complementary to a target having a second nucleic acid sequence, a first and a second interactive labels, a 5' end and a 3' end, and one or more photocleavable moieties coupled to one or more nucleotides of the specific hydrolysis probe, wherein the photocleaveable moiety interferes with the hybridization of the specific hydrolysis probe with the region of the amplification product. Also disclosed are PCR methods for the detection of the presence or absence of a target nucleic acid in a sample utilizing the photoblocked probes, as well as kits.

10 Claims, 1 Drawing Sheet

PHOTOBLOCKED PROBES AND METHODS FOR SEQUENTIAL DETECTION OF NUCLEIC ACIDS

FIELD OF THE INVENTION

The present invention relates to the field of polymerase chain reaction (PCR) based diagnostic, and more particularly, to PCR detection methods utilizing photoblocked probes.

BACKGROUND OF THE INVENTION

PCR is an efficient and cost effective way to copy or 'amplify' small segments of DNA or RNA. Using PCR, millions of copies of a section of DNA are made in just a few hours, yielding enough DNA required for analysis. This method allows clinicians to diagnose and monitor diseases using a minimal amount of sample, such as blood or tissue. Real-time PCR allows for amplification and detection to occur at the same time. One method of detection is done by utilizing oligonucleotide hydrolysis probes (also known as TaqMan® probes) having a fluorophore covalently attached, e.g., to the 5' end of the oligonucleotide probe and a quencher attached, e.g., internally or at the 3' end. Hydrolysis probes are dual-labeled oligonucleotide probes that rely on the 5' to 3' nuclease activity of Taq polymerase to cleave the hydrolysis probe during hybridization to the complementary target sequence, and result in fluorescent based detection.

Many real time PCR methods are currently limited by the fact that only one target nucleic acid sequence can be analyzed in a single closed reaction vessel, sometimes called the one-channel-one-target limitation. PCR detection methods that allow analysis of a greater number of targets in a single tube would provide additional capability and also provide more efficient detection testing methods. Thus, there is a need in the art for a quick and reliable method to detect two or more target nucleic acids in a single closed reaction, and the present disclosure provides benefits and solutions.

SUMMARY OF THE INVENTION

The present disclosure relates to photoblocked probes which include reversibly attached photocleavable moieties that inhibit the photoblocked probes from hybridization with their targets. Methods and kits are also disclosed which can utilize the photoblocked probes for detecting one or more target nucleic acids in a sample.

In one embodiment, a photoblocked probe is provided including a hydrolysis probe having a first nucleic acid sequence complementary to a target having a second nucleic acid sequence; a first and a second interactive label; a 5' end and a 3' end; and one or more photocleavable moieties coupled to one or more nucleotides of the hydrolysis probe, the photocleavable moiety configured to interfere with hybridization of the first nucleic acid sequence with the second nucleic acid sequence.

In one embodiment, a method for detecting a target nucleic acid in a sample is provided, the method including performing an amplifying step including contacting a sample with at least one primer having a first nucleic acid sequence to produce an amplification product if any target nucleic acid is present in the sample; performing at least a first hybridizing step including contacting the amplification product with a specific hydrolysis probe having a second nucleic acid sequence complementary to a region of the amplification product, the first specific hydrolysis probe having a first and a second interactive label, a 5' end and a 3' end, and one or more photocleavable moieties coupled to one or more nucleotides of the specific hydrolysis probe, wherein the photocleaveable moiety interferes with the hybridization of the specific hydrolysis probe with the region of the amplification product; cleaving the photocleavable moiety from the specific hydrolysis probe by introducing a light having a wavelength effective to cleave the photocleavable moiety from the specific hydrolysis probe; and detecting the presence or absence of the amplification product, wherein the presence of the amplification products is indicative of the target nucleic acid target, and wherein the absence of the amplification products is indicative of the absence of the target nucleic acid.

In another embodiment, a kit for detecting a target nucleic acid in a sample is provided, including at least one primer having a first nucleic acid sequence specific to produce an amplification product of the target nucleic acid; and a specific hydrolysis probe having a second nucleic acid sequence complementary to a region of the amplification product, the specific hydrolysis probe including a first and a second interactive label, a 5' end and a 3' end, and one or more photocleavable moieties coupled to one or more nucleotides of the specific hydrolysis probe, wherein the photocleaveable moiety interferes with the hybridization of the specific hydrolysis probe with the region of the amplification product.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
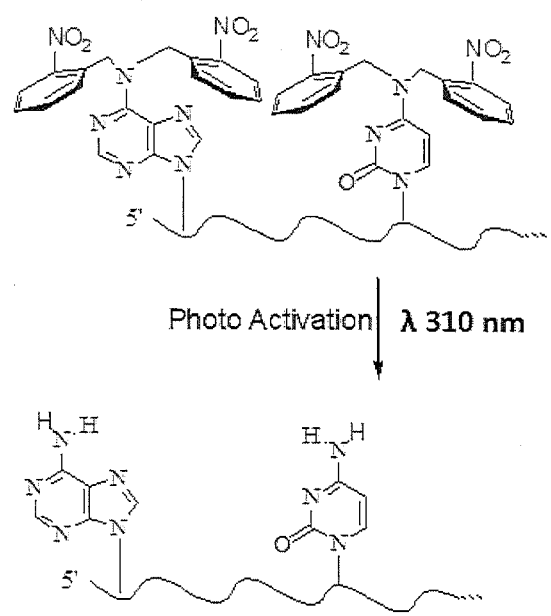
FIG. 1 shows a schematic view of a probe having photocleavable moieties coupled to certain nucleotides which are cleaved upon photo activation.
Figure 2:
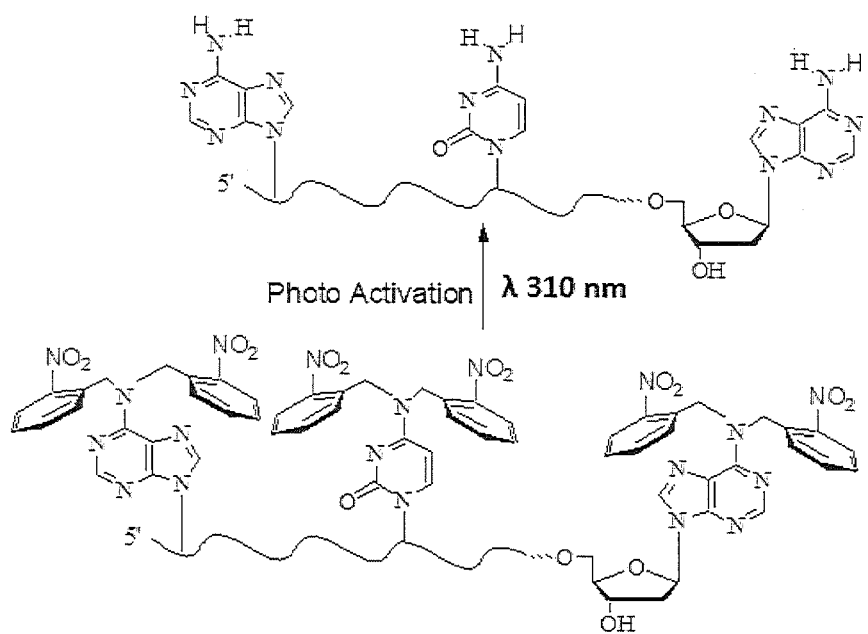
FIG. 2 shows a schematic view of a probe having photocleavable moieties coupled to certain nucleotides which are cleaved upon photo activation.

Photoblocked probes, methods, and kits for detecting a target nucleic acid in a sample are described herein. The increased number of target detection capability and sensitivity of real-time PCR for detection of multiple target nucleic acids compared to other methods, as well as the improved features of real-time PCR including sample containment and real-time detection of the amplified product, make feasible the implementation of this technology for routine diagnosis and detection of one or more target nucleic acids in the clinical laboratory.

The subject matter of the present disclosure includes detection probes, for example hydrolysis probes including a reporter moiety and quencher moiety wherein the hydrolysis probes can be hydrolyzed or degraded by enzyme and signal is generated. The hydrolysis probes can be photoblocked with a photocleavable moiety that are effective to keep the photoblocked probes off the target nucleic acid. By keeping the photoblocked hydrolysis probe off the target, the enzyme is not able to degrade the photoblocked probe. The degradation of the probes can be delayed until a desired or predetermined time, thus delaying the production of signal (s) in connection with the degradation of the respective photoblocked probes. The photoblocked probes are inhibited from hybridization with their targets because the photocleavable moieties are designed to interfere with hybridization of the complementary nucleic acid sequences of the probe and its target. The photocleavable moiety can be selected to be cleaved, i.e., decoupled, from the probe with a light of a certain wavelength, for example a wavelength of between about 200 nm to about 450 nm, e.g., between about 200 nm to about 300 nm, or e.g., between about 280 nm to about 315 nm, or e.g., between about 300 nm to about 400 nm, or e.g., between about 315 nm to about 415 nm. The term "about" in the context of a stated wavelength may include exactly the stated wavelength, and also include a wavelength having 1 nm, 2 nm, 3 nm, 4=, or 5 nm, plus or minus the stated wavelength. Thus, when a light of appropriate wavelength is introduced, e.g., by shining or flashing, to the photoblocked probe, the photocleavable moiety is cleaved from the probe which removes the interference with hybridization. The introduction of the light can be manual or automated. Once the light is introduced and the photocleavable moieties are removed, the probe is free to hybridize with its target. The probe and target can form a double stranded stretch of DNA which can become a substrate for the polymerase during the PCR reaction. The nuclease activity of the polymerase can degrade the hybridized probe, separating the reporter and quencher, and generating a detectable signal.

The probes described herein can be designed with a variety of different photocleavable moieties that require only a light of a specific wavelength for their cleavage (Bochet, 2002, "Photolabile Protecting Groups and Linkers", J. Chem. Soc., Perkins Trans. 1, 125-142). Furthermore, the probes can be designed for a multiplexed PCR reaction where different photocleavable moieties are used which cleave upon the introduction of lights of different wavelengths. For example a first photoblocked probe can include a first photocleavable moiety that is cleavable by irradiation of a light of a first specific wavelength, and a second photoblocked probe can include a second photocleavable moiety that is cleavable by irradiation of a light having a second specific wavelength. It is important that the first and the second cleavable moieties are chosen to have selective and sequential photochemical reactions initiated by lights of specific wavelengths, such that the photocleavable moieties are not photocleaved in the presence of the other due to their absorbing light in the same general spectra range (Leminex et al., 2006 "Selective and Sequential Photorelease Using Molecular Switches", Angew. Chem., 118:6974-6978). The multiplexed PCR reaction can also include at least one non-photoblocked probe which can be utilized for the first PCR reaction to detect the presence or absence of the first target nucleic acid, followed by one or more different photoblocked probes for sequential PCR reactions to detect the presence or absence of the second and the third target nucleic acids in the sample.

One aspect of the present disclosure involves the inclusion of modified nucleotides into oligonucleotide probes. Previous data has shown the possibility of initiating PCR by the removal of o-Nitrobenzyl groups from the exocyclic amines of the bases at the 3'-end of PCR primers, at the beginning of the PCR process (see, e.g., U.S. Pat. No. 6,001,611, Young, et al., Light triggered polymerase chain reaction, Chem. Commun 2008: p. 462-464, and US2008/0009007). The present disclosure makes use of a different property of such modified nucleotides, in that the inclusion of the modifiers prevents hybridization of the modified oligonucleotide probe to its complementary sequence, due to interference with the normal Watson-Crick base pairing of DNA bases. As such, these oligonucleotide probes are non-functional partners in an initial PCR reaction. At a suitable, user-selectable time in the PCR process, illumination of the PCR reaction products with a light having a predefined and proper wavelength removes the photocleavable protecting groups, thus allowing hybridization of the oligonucleotide probes to their complementary targets. This can be useful in effectively removing an oligonucleotide probe (e.g., a TaqMan probe) from active participation during an initial round of amplification. Upon photorelease, the fully effective probe can participate in signal generation, e.g., in a second round of amplification. A multiplexed PCR reaction can be designed such that two different oligonucleotide probes are modified with two different photocleavable moieties that have different photolysis rates and are activated at two different specific wavelengths. The multiplexed PCR reaction can start with first round of amplification using a regular probe that is not modified with any photocleavable moieties, followed by second round of PCR amplification and irradiation of a first light having a first specific wavelength which deprotects or removes the photocleavable moiety from a second probe that is modified with a first type of photocleavable moieties, and this can be followed with a third round of PCR amplification and irradiation of a second light having a second specific wavelength which deprotects or removes the photocleavable moiety from a second probe that is modified with a second type of photocleavable moieties. The signal generation can take place in the same channel as a prior amplification and detection. For example, positive results for two unique targets in the same detection channel can be indicated by a biphasic growth curve, with curves generated both before and after illumination. This would serve to extend the multiplicity of detection of multiple targets in PCR.

The "photocleavable moiety" discussed herein have several synonymous words in the literature and can also be referred to as "photoremovable groups", "photoblocking groups", "phototriggers", "caged compounds", "photolabile groups", and other similar terms. One advantage of employing a photocleavable moiety is the ability to perform reactions with high selectivity at very mild reaction conditions. A number of different types of photocleavable moieties are available and can be used in the context of the present disclosure. For example, the use of ortho-nitrobenzyl derivatives as protecting groups for amines and alcohols is well known, e.g., 2-nitrobenzyl, 1-(4,5-dimethoxy-2-nitrophenyl)diazoethane (DMNPE), nitroveratryl, 1-pyrenylmethyl, 2-oxymethylene anthraquinone, 5-bromo-7-nitroindolinyl, 2-nitro-4-bromobenzyl bromide, 2-nitro-4,5-(dimethoxy) benzyl bromide, o-hydroxy-alpha-methyl cinnamoyl and mixtures thereof. Such modifications are stable to the conditions of chemical DNA synthesis which render them attractive for incorporation into oligonucleotides.

The methods descried herein may include performing at least one cycling step that includes amplifying one or more portions of one or more target nucleic acid molecules, e.g., one or more gene targets, and/or one or more Single Nucleotide Polymorphisms (SNPs), in a sample using one or more primers or one or more primer pairs. As used herein, "primer", "primers", and "primer pairs" refer to oligonucleotide primer(s) that specifically anneal to the nucleic acid sequence target, and initiate DNA synthesis therefrom under appropriate conditions. Each of the primers anneals to a region within or adjacent to the respective target nucleic acid molecule such that at least a portion of each amplification product contains nucleic acid sequence corresponding to respective targets and/or SNPs, if present. An amplification product is produced provided that the target nucleic acid is present in the sample.

The method can also include a hybridizing step that includes contacting the amplification product with one or more photoblocked probe including a first nucleic acid sequence complementary to a region of the amplification product, i.e., a target having a second nucleic acid sequence. The photoblocked probe may be a hydrolysis probes and can include a first and a second interactive label, a 5' end and a 3'end, and a photocleavable moiety coupled to a nucleic acid of the specific hydrolysis probe, the photocleavable moiety configured to interfere with hybridization of the first nucleic acid sequence with the second nucleic acid sequence. In some embodiments, the photocleavable moiety can be attached one or more nucleotides, e.g., to adenine (A), thymine (T), guanine (G), and cytosine (C). In some embodiments, the photocleavable moiety can be attached to the phosphate back bone of the probe.

The heterocyclic bases of nucleosides are suitable for the attachment of such photocleavable moieties. U.S. Pat. No. 6,001,611 discloses methods of attachment of the ortho-nitrobenzyl group to the exocyclic amine of deoxyadenosine oligonucleotides. From this example it was shown that the ortho-nitrobenzyl group can be incorporated either one or two times on the amine group to generate mono- or bis-ortho-nitrobenzyl adenosine. These compounds were further elaborated into synthetic oligonucleotides. In this example, the bis-ortho-nitrobenzyl derivative did not allow successful. PCR amplification to take place, until after the ortho-nitrobenzyl groups were removed by UV light exposure. This supports the presently disclosed subject matter in that the bis-ortho-nitrobenzyl derivatized oligonucleotide would significantly interfere with oligonucleotide hybridization, preventing hybridization and subsequent PCR, until the ortho-nitrobenzyl groups were removed.

The exocyclic amines of the DNA bases of cytosine and guanosine are similarly suitable for the attachment of ortho-nitrobenzyl group and other types of photocleavable modifiers. These modified nucleosides, when incorporated into oligonucleotides, would also significantly interfere with the ability of the oligonucleotides to form stable hybrid structures with substantially complementary sequences.

Thymidine does not have an analogous exocyclic amine suitable for derivatization, but the base is nevertheless a suitable substrate for the attachment of photocleavable moieties through reaction of the enol form of the base to allow for attachment at either the $O^4$-position or the $N^3$-position of the thymine base.

Attachment of analogous photocleavable groups has been reported by Ghosn, et al., *Control of DNA Hybridization with Photocleavable Adducts*, Photochem. Photobiol., 2005, 81:953-959, wherein ester bonds between the phosphate backbone of DNA oligonucleotides and a photocleavable group through the intermediacy of a reactive diazoethane derivative (DMNPE). This is a viable method for the introduction of ortho-nitrobenzyl groups into oligonucleotides by such post synthesis modification.

In order to detect whether or not the target nucleic acid of interest is present or absent in the sample, the amplification product is detected by way of the detectable label being released from the specific probe. If the amplification product is detected by way of the specific probe, the presence of the target nucleic acid is indicated. If alternatively, the amplification product is not detected by way of the specific probe, the presence of the target nucleic acid is not indicated. Thus, the presence of the amplification products is indicative of the presence of the target nucleic acid target, and the absence of the amplification products is indicative of the absence of the target nucleic acid target.

As used herein, the term "amplifying" refers to the process of synthesizing nucleic acid molecules that are complementary to one or both strands of a template nucleic acid molecule (e.g., target nucleic acid molecules for Human immunodeficiency virus (HIV) or *Mycobacterium tuberculosis* (MTB), or Hepatitis C virus (HCV), or other target nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. In general, primers are designed based on known template sequences. One primer primes the sense strand, and the other primes the complementary strand of the target DNA or cDNA. PCR can be performed on a uniform target DNA or RNA (i.e., targets with the same sequence) or on mixed target DNAs or RNAs, (i.e., targets with different intervening sequences flanked by conserved sequences). For mixed DNAs/RNAs (e.g., containing sequence heterogeneity) even mismatched primers can function in the PCR reaction if the sequences of the targets have enough complementarity to the mismatched primers (i.e., tolerant primers).

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the present disclosure are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

The term "photocleavable moiety" or other synonymous terms refer to chemical compounds that can be broken down by photons. Certain photocleavable moieties form covalent bonds that can be cleaved with exposure to radiation, e.g., a certain wavelength of light. Photocleavable compounds play an important role as protecting groups in blocking functional groups present in nucleosides, nucleotides, sugars and amino acids, which are used for the synthesis of biomolecules, e.g. nucleic acids and their derivatives, proteins, peptides and carbohydrates. Such compounds have the advantage that deprotection of the protected functional group can be performed simply via light exposure. Therefore, photocleavable compounds provide the basis for the photolithography based spatially resolved synthesis of oligonucleotides or peptides on solid supports, such as microarrays. The use of photolabile compounds for the synthesis of microarrays is well known (Pease, et al. Proc. Natl. Acad. Sci. USA 91 (1994) 5022-5026), Hasan, et al. Tetrahedron 53 (1997) 4247-4264).

The term "photoblocked" refers to the state of being blocked with a photocleavable moiety which can be removed by introduction of a light of proper wavelength.

The photocleavable moieties described herein can be activated with a light in the ultraviolet (UV) and near UV-range (for example about 250-400 nm, e.g., about 254-365 nm) to cleave the covalent bond(s) in order to cleave the photocleavable moieties. Light sources, which are suitable to generate such wavelength, are, e.g., mercury arc lamps, excimer lasers, UV-LEDs, and frequency multiplied solid-state lasers.

Target Nucleic Acids and Oligonucleotides

The present description provides methods to a target nucleic acid by amplifying, for example, a portion of the target nucleic acid sequences, which may be any target nucleic acid sequence, for example target nucleic acid sequences from, e.g., HIV, HCV, or MTB that is rifampicin resistant.

For detection of the target nucleic acid sequence, primers and probes to amplify the target nucleic acid sequences can be prepared. Also, functional variants can be evaluated for specificity and/or sensitivity by those of skill in the art using routine methods. Representative functional variants can include, e.g., one or more deletions, insertions, and/or substitutions in the primers and/or probes disclosed herein. For example, a substantially identical variant of the primers or probes can be provided in which the variant has at least, e.g., 80%, 90%, or 95% sequence identity to one original primers and probes, or a complement thereof.

A functionally active variant of any of primer and/or probe may be identified which provides a similar or higher specificity and sensitivity in the presently described-methods, kits, or probes as compared to the respective original sequences.

As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify the target nucleic acid sequences can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the present methods may use one or more probes in order to detect the presence or absence of a target nucleic acid sequence in a sample. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids". A "probe" can be referred to as a "detection probe" meaning that it detects the target nucleic acid.

In some embodiments, the described probes can be labeled with at least one fluorescent label. In one embodiment probes can be labeled with a donor fluorescent moiety, e.g., a fluorescent dye, and a corresponding acceptor fluorescent moiety, e.g., a quencher.

Designing oligonucleotides to be used as TaqMan hydrolysis probes can be performed in a manner similar to the design of primers. Embodiments may use a single probe for detection of the amplification product. Depending on the embodiment, the probe may include at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Polymerase Chain Reaction (PCR)

U.S. Pat. Nos. 4,683,202; 4,683,195; 4,800,159; and 4,965,188 disclose conventional PCR techniques. U.S. Pat. Nos. 5,210,015; 5,487,972; 5,804,375; 5,804,375; 6,214,979; and 7,141,377 disclose real-time PCR and TaqMan® techniques. PCR typically employs two oligonucleotide primers that bind to a selected nucleic acid template (e.g., DNA or RNA). Primers useful in the described embodiments include oligonucleotides capable of acting as points of initiation of nucleic acid synthesis within the target nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the target nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ target nucleic acid such as RNA or DNA (cDNA). The template nucleic acid need not be purified; it may be a minor fraction of a complex mixture, such as target nucleic acid contained in human cells. Target nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM MgCl$_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, a oligonucleotide probe can contain a donor fluorescent moiety and a corresponding quencher, which may or not be fluorescent, and which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' nuclease activity of, e.g., a Taq polymerase such that the fluorescent emission of the donor fluorescent moiety is no longer quenched. Exemplary probes for this purpose are described in, e.g., U.S. Pat. Nos. 5,210,015; 5,994,056; and 6,171,785. Commonly used donor-acceptor pairs include the FAM-TAMRA pair. Commonly used quenchers are DABCYL and TAMRA. Commonly used dark quenchers include Black-Hole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodaminexisothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present disclosure is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of a Target Nucleic Add

The present disclosure provides methods for detecting the presence or absence of a target nucleic acid in a biological sample. Methods provided avoid problems of sample contamination, false negatives, and false positives. The methods include performing at least one cycling step that includes amplifying a portion of the target nucleic acid molecule from a sample using a primer pair, and a fluorescent detecting step. Multiple cycling steps may be performed, preferably in a thermocycler. The described methods can be performed using the primers and probes to detect the presence of the target nucleic acid in the sample.

As described herein, amplification products can be detected using labeled hybridization probes that take advantage of FRET technology. One FRET format utilizes TaqMan® technology to detect the presence or absence of an amplification product, and hence, the presence or absence of the target nucleic acid. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of the target nucleic acid in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of the target nucleic acid). If amplification of the target nucleic acid occurs and an amplification product is produced, the step of hybridizing results in a detectable signal based upon FRET between the members of the pair of probes.

Generally, the presence of FRET indicates the presence of the target nucleic acid in the sample, and the absence of FRET indicates the absence of the target nucleic acid the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of the presence of the target nucleic acid in a sample.

Representative biological samples that can be used in practicing the disclosed methods include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release target nucleic acid or in some cases, the biological sample can be contacted directly with the PCR reaction components and the appropriate oligonucleotides.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996; 5,683,896; and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

It is understood that the embodiments of the present disclosure are not limited by the configuration of one or more commercially available instruments.

Articles of Manufacture/Kits

The present disclosure further provides for articles of manufacture or kits to detect a target nucleic acid. An article of manufacture can include primers and probes used to detect the target nucleic acid, together with suitable packaging materials. Representative primers and probes for detection of the target nucleic acid are capable of hybridizing to the target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to a target nucleic acid target nucleic acid molecules are provided.

Articles of manufacture of the present disclosure can also include one or more fluorescent moieties for labeling the probes or, alternatively, the probes supplied with the kit can be labeled. For example, an article of manufacture may include a donor and/or an acceptor fluorescent moiety for labeling target nucleic acid specific probes. Examples of suitable FRET donor fluorescent moieties and corresponding acceptor fluorescent moieties are provided above.

Articles of manufacture can also contain a package insert or package label having instructions thereon for using the primers and probes to detect a target nucleic acid in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present invention will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example I

Photocleavable Moiety Attached to the Base

A target nucleic acid may be detected in a sample by way of a detection method including an amplifying step which can be performed by contacting a sample with at least one primer having a first nucleic acid sequence to produce an amplification product if any target nucleic acid is present in the sample.

At least a first hybridizing step can be performed by contacting the amplification product with a specific hydrolysis probe having a second nucleic acid sequence complementary to a region of the amplification product, the first specific hydrolysis probe including a first and a second interactive label, a 5' end and a 3' end, and one or more photocleavable moieties coupled to one or more nucleotides of the specific hydrolysis probe, wherein the photocleavable moiety interferes with the hybridization of the specific hydrolysis probe with the region of the amplification product.

The photocleavable moieties may be coupled to one or more of the bases in the sequence of the specific hydrolysis probe. The photocleavable moiety may be 2-nitrobenzyl, 2-nitro-4-bromobenzyl, and 2-nitro-4,5-(dimethoxy)benzyl, and may be coupled to the base by way of introduction of these photocleavable moieties into the bases of nucleosides using standard organic chemistry techniques familiar to the skilled artisan. These modified nucleosides can be further elaborated into reagents suitable for automated oligonucleotide synthesis, for example, as standard phosphoramidite reagents. These phosphoramidites can be incorporated into oligonucleotides at defined positions in the oligonucleotides at the discretion of the user, either singly or multiply, and in combination with other nucleoside phosphoramidites which would deliver a second photocleavable moiety.

The detection method may also include the step of cleaving the photocleavable moiety from the specific hydrolysis probe by introducing a light having a wavelength effective to cleave the photocleavable moiety from the specific hydrolysis probe. For example, with respect to 2-nitrobenzyl the light can have a wavelength of 310 nm, with respect to 2-nitro-4-bromobenzyl the light can have a wavelength of about 254 nm, and with respect to 2-nitro-4,5-(dimethoxy)benzyl the light can have a wavelength of about 419 nm.

The detection method may include a step of detecting the presence or absence of the amplification product, wherein the presence of the amplification products is indicative of the target nucleic acid target, and wherein the absence of the amplification products is indicative of the absence of the target nucleic acid.

Example II

Photocleavable Moiety Attached to the Phosphate Group

A target nucleic acid may be detected in a sample by way of a detection method including an amplifying step which can be performed by contacting a sample with at least one primer having a first nucleic acid sequence to produce an amplification product if any target nucleic acid is present in the sample.

At least a first hybridizing step can be performed by contacting the amplification product with a specific hydrolysis probe having a second nucleic acid sequence complementary to a region of the amplification product, the first specific hydrolysis probe including a first and a second interactive label, a 5' end and a 3' end, and one or more photocleavable moieties coupled to one or more nucleotides of the specific hydrolysis probe, wherein the photocleaveable moiety interferes with the hybridization of the specific hydrolysis probe with the region of the amplification product.

The photocleavable moieties may be coupled to one or more of the phosphate groups in the sequence of the specific hydrolysis probe. The photocleavable moiety may be 1-(4,5-dimethoxy-2-nitrophenyl)ethyl, and may be coupled to the phosphate group by way of the method described in Ghosn et al., et al., *Control of DNA Hybridization with Photocleavable Adducts*, Photochem. Photobiol., 2005, 81:953-959. Specifically, a reactive diazoalkane derivative can be produced by the oxidation of suitable hydrazones. This diazoalkane derivative can be reacted with a preformed synthetic oligonucleotide, whereby the diazoalkane moiety reacts with the phosphate groups in the backbone of the synthetic DNA.

The detection method may also include the step of cleaving the photocleavable moiety from the specific hydrolysis probe by introducing a light having a wavelength effective to cleave the photocleavable moiety from the specific hydrolysis probe. For example, with respect to 1-(4,5-dimethoxy-2-nitrophenyl)ethyl the light can have a wavelength of about 365 nm.

The detection method may include a step of detecting the presence or absence of the amplification product, wherein the presence of the amplification products is indicative of the target nucleic acid target, and wherein the absence of the amplification products is indicative of the absence of the target nucleic acid.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A photoblocked probe comprising:
   a hydrolysis probe comprising a first nucleic acid sequence complementary to a target comprising a second nucleic acid sequence;
   a first and a second interactive label;
   a 5' end and a 3' end; and
   one or more photocleavable moieties coupled to one or more nucleotides of the hydrolysis probe, the photocleavable moiety configured to interfere with hybridization of the first nucleic acid sequence with the second nucleic acid sequence;
   wherein the photocleavable moiety is attached to the exocyclic amine of adenosine, guanosine and cytidine, and wherein the photocleavable moiety is selected from the group consisting of nitroveratryl, 1-pyrenylmethyl, 2-oxymethylene anthraquinone, 5-bromo-7-nitroindolinyl, 2-nitro-4-bromobenzyl, 2-nitro-4,5-(dimethoxy)benzyl, o-hydroxy-alpha-methyl cinnamoyl, and mixtures thereof.

2. The photoblocked probe of claim 1, wherein the first interactive label comprises a donor fluorescent moiety at the 5' end, and the second interactive label comprises a corresponding acceptor fluorescent moiety within no more than 8 nucleotides of the donor fluorescent moiety on the hydrolysis probe.

3. A method for detecting a target nucleic acid in a sample, the method comprising:
   performing an amplifying step comprising contacting a sample with at least one primer comprising a first nucleic acid sequence to produce an amplification product if any target nucleic acid is present in the sample;
   performing at least a first hybridizing step comprising contacting the amplification product with a specific hydrolysis probe comprising a second nucleic acid sequence complementary to a region of the amplification product, the first specific hydrolysis probe comprising a first and a second interactive label, a 5' end and a 3' end, and one or more photocleavable moieties coupled to one or more nucleotides of the specific hydrolysis probe, wherein the photocleaveable moiety interferes with the hybridization of the specific hydrolysis probe with the region of the amplification product;
   cleaving the photocleavable moiety from the specific hydrolysis probe by introducing a light having a wavelength effective to cleave the photocleavable moiety from the specific hydrolysis probe; and
   detecting the presence or absence of the amplification product, wherein the presence of the amplification products is indicative of the target nucleic acid target, and wherein the absence of the amplification products is indicative of the absence of the target nucleic acid;
   wherein the photocleavable moiety is attached to the exocyclic amine of adenosine, guanosine and cytidine, and wherein the photocleavable moiety is selected from the group consisting of nitroveratryl, 1-pyrenylmethyl, 2-oxymethylene anthraquinone, 5-bromo-7-nitroindolinyl, 2-nitro-4-bromobenzyl, 2-nitro-4,5-(dimethoxy)benzyl, o-hydroxy-alpha-methyl cinnamoyl, and mixtures thereof.

4. The method of claim 3, wherein the first interactive label comprises a donor fluorescent moiety at the 5' end, and the second interactive label comprises a corresponding acceptor fluorescent moiety within no more than 8 nucleotides of the donor fluorescent moiety on the hydrolysis probe.

5. The method of claim 3, wherein the amplification employs a polymerase enzyme having 5' to 3' nuclease activity.

6. The method of claim 3, further comprising:
   performing a second amplifying step comprising contacting the sample with at least a second primer comprising a third nucleic acid sequence to produce a second amplification product if any second target nucleic acid is present in the sample;
   performing at least a second hybridizing step comprising contacting the second amplification product with a second specific hydrolysis probe comprising a fourth nucleic acid sequence complementary to a region of the second amplification product, the second specific hydrolysis probe comprising a third and a fourth interactive label, a second 5' end and a second 3' end, and one or more second photocleavable moieties coupled to one or more nucleotides of the second specific hydrolysis probe, wherein the second photocleaveable moiety interferes with the hybridization of the second specific hydrolysis probe with the region of the second amplification product;
   cleaving the second photocleavable moiety from the second specific hydrolysis probe by introducing a second light having a second wavelength effective to cleave the second photocleavable moiety from the second specific hydrolysis probe, such that the second photocleavable moiety is not cleaved while the first light having the first wavelength is introduced to cleave the first photocleavable moiety from the first specific hydrolysis probe; and
   detecting the presence or absence of the second amplification product, wherein the presence of the second amplification products is indicative of the second target nucleic acid, and wherein the absence of the second amplification products is indicative of the absence of the second target nucleic acid.

7. The method of claim 6, wherein the first photocleavable moiety is 2-nitro-4-bromobenzyl, and the second photocleavable moiety is 2-nitro-4,5-(dimethoxy)benzyl.

8. A kit for detecting a target nucleic acid in a sample, comprising:
   at least one primer comprising a first nucleic acid sequence specific to produce an amplification product of the target nucleic acid; and a specific hydrolysis probe comprising a second nucleic acid sequence complementary to a region of the amplification product, the specific hydrolysis probe comprising a first and a second interactive label, a 5' end and a 3' end, and one or more photocleavable moieties coupled to one or more nucleotides of the specific hydrolysis probe, wherein the photocleaveable moiety interferes with the hybridization of the specific hydrolysis probe with the region of the amplification product;

wherein the photocleavable moiety is attached to the exocyclic amine of adenosine, guanosine and cytidine, and wherein the photocleavable moiety is selected from the group consisting of nitroveratryl, 1-pyrenylmethyl, 2-oxymethylene anthraquinone, 5-bromo-7-nitroindolinyl, 2-nitro-4-bromobenzyl, 2-nitro-4,5-(dimethoxy)benzyl, o-hydroxy-alpha-methyl cinnamoyl, and mixtures thereof.

9. The kit of claim 8, wherein the first interactive label comprises a donor fluorescent moiety at the 5' end, and the second interactive label comprises a corresponding acceptor fluorescent moiety within no more than 8 nucleotides of the donor fluorescent moiety on the hydrolysis probe.

10. The kit of claim 8, further comprising a polymerase enzyme having 5' to 3' nuclease activity.

\* \* \* \* \*